(12) United States Patent
Ardizzone et al.

(10) Patent No.: US 7,507,198 B2
(45) Date of Patent: ***Mar. 24, 2009

(54) BI-AXIAL ROTATING MAGNETIC THERAPEUTIC DEVICE

(76) Inventors: Vincent Ardizzone, 9 Stuarts Ct., Port Jefferson, NY (US) 11777; Thomas Bove, 17625 E. Euclid, Spokane, WA (US) 99216

( * ) Notice: Subject to any disclaimer, the term of this patent is extended or adjusted under 35 U.S.C. 154(b) by 490 days.

This patent is subject to a terminal disclaimer.

(21) Appl. No.: 10/506,125

(22) PCT Filed: Nov. 20, 2002

(86) PCT No.: PCT/US02/37587

§ 371 (c)(1),
(2), (4) Date: Aug. 27, 2004

(87) PCT Pub. No.: WO03/074124

PCT Pub. Date: Sep. 12, 2003

(65) Prior Publication Data

US 2005/0124847 A1    Jun. 9, 2005

Related U.S. Application Data

(63) Continuation-in-part of application No. 10/087,135, filed on Feb. 28, 2002, now Pat. No. 6,648,812.

(60) Provisional application No. 60/272,384, filed on Feb. 28, 2001.

(51) Int. Cl.
*A61N 2/06* (2006.01)

(52) U.S. Cl. ......................................................... 600/9

(58) Field of Classification Search .................. 600/11, 600/9, 12, 15; 601/1, 15, 18, 19, 22, 27–32, 601/49, 50, 52, 54, 61, 63, 64, 110–113, 601/117–119, 122, 127–131; D24/211; 33/323; 701/220; 361/141; 335/216; 505/851, 879; 244/175; 250/203.6
See application file for complete search history.

(56) References Cited

U.S. PATENT DOCUMENTS 4,162,675 A     7/1979  Kawada ........................ 128/55

(Continued)

FOREIGN PATENT DOCUMENTS

DE            25 10 173        9/1976

(Continued)

*Primary Examiner*—Samuel G Gilbert
(74) *Attorney, Agent, or Firm*—Cislo & Thomas, LLP

(57) ABSTRACT

A device for applying a time-varying magnetic field to a human or animal body for therapeutic purposes comprising a magnetic body (72), housed in a free moving member (80), which is it-self housed within the device. The device is powered by a small electric motor that drives the free moving member (80) and magnetic body (72) to rotate about an axis of first rotation. The magnetic body is further caused to rotate around an axis of second rotation through angular forces imparted on it either mechanically or magnetically. Mechanical angular force is imparted by a gear and tooth arrangement or other similar tactile interaction with a roller member (106). Magnetic angular force is imparted by stationary magnets (110) as the magnetic body (72) rotates past them. The two rotational movements of the magnetic body (72) are oblique to one another and produce both a time-varying field of magnetic flux density and a time varying field of angular flux displacement.

15 Claims, 15 Drawing Sheets

U.S. PATENT DOCUMENTS

| | | | | |
|---|---|---|---|---|
| 4,727,857 A | 3/1988 | Hörl | ............................ | 128/1.3 |
| 4,744,350 A | 5/1988 | Sato | ............................ | 128/57 |
| 4,846,159 A | 7/1989 | Anzai et al. | .................... | 128/57 |
| 5,152,281 A | 10/1992 | Koll | ............................ | 128/57 |
| 5,632,720 A | 5/1997 | Kleitz | ........................ | 601/15 |
| 5,667,469 A * | 9/1997 | Zhang et al. | .................... | 600/9 |
| 6,001,055 A | 12/1999 | Souder | ........................ | 600/9 |
| 6,102,875 A | 8/2000 | Jones | ........................ | 601/113 |

FOREIGN PATENT DOCUMENTS

| | | |
|---|---|---|
| EP | 0253 398 B1 | 3/1993 |
| FR | 2789893 | 2/1999 |
| JP | 04-53567 | 2/1992 |
| WO | WO82/03177 | 9/1982 |

\* cited by examiner

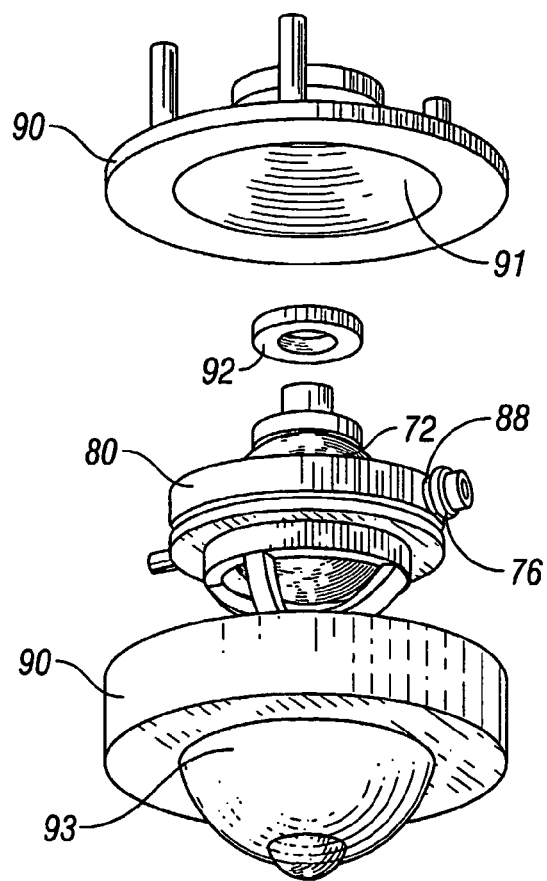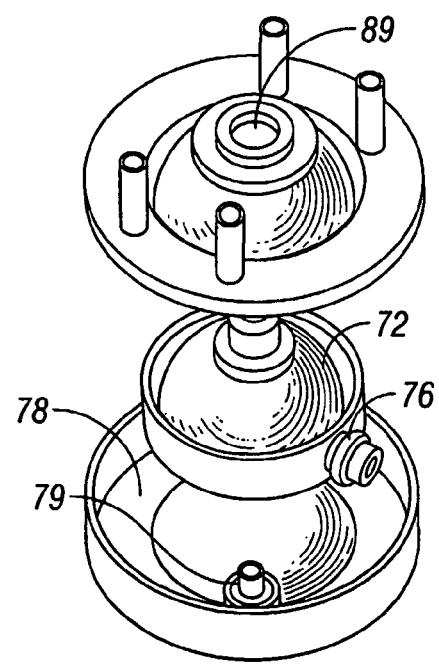
FIG. 9    FIG. 10

BI-AXIAL ROTATING MAGNETIC THERAPEUTIC DEVICE

CROSS-REFERENCES TO RELATED APPLICATIONS

This application claims the benefit of International Publication No. WO 03/74124, filed Nov. 20, 2002, and also is a continuation-in-part of U.S. patent application Ser. No. 10/087,135, filed Feb. 28, 2002, now U.S. Pat. No. 6,648,812, which is incorporated by reference as if fully stated herein, and which claims the benefit of U.S. Provisional Patent Application Ser. No. 60/272,384 filed Feb. 28, 2001.

TECHNICAL FIELD

This invention relates generally to a magnetic field generating apparatus and more specifically to a magnetic field generating apparatus that produces a time-varying angular displacement of magnetic flux density for use in therapeutic applications on humans or on animals.

BACKGROUND ART

Various devices have been made to create time-varying magnetic fields for use on the human body. Generally, two types of time-varying magnetic fields have been used. The first type used an alternating current ("AC") field that is produced when electric current is caused to alternate at any given frequency. In accordance with Maxwell's equations, a magnetic field is concurrently produced at the same frequency as the electric field. Included in this first type of time-varying magnetic field device are pulsed electromagnetic fields (PEMF) which are generated when a current is caused to move through a conductor in discrete impulses of electric charge moving in the same direction.

A second general type of device for creating time-varying magnetic fields involves physically moving a static magnetic field through space. While linear displacement is one way to accomplish this, another common method involves rotating the static magnetic field. The source of the static magnetic field is generally a permanent magnet, since an electromagnet requires considerable expenditure of energy in the form of current generation and the subsequent dissipation of unwanted heat energy.

The therapeutic uses of time-varying magnetic fields have been described and clinically evaluated in numerous literature. The more popular publications written for the general public include "Magnetic Therapy" by Dr. Ronald Lawrence and Dr. Paul Rosch, "The Pain Relief Breakthrough" by Dr. Julian Whitaker and Brenda Adderly, and "Magnetic Therapy in Eastern Europe" by Dr. Jiri Jerabek and Dr. William Pawluk. These books offer numerous references to clinical studies which purport to show the effectiveness of time-varying magnetic fields for the treatment of a multitude of chronic and acute conditions including atherosclerosis, carpal tunnel syndrome, chronic bronchitis, post-ischemic injury, edema, fractures, infected wounds, limb grafts, burns, scars, macular degeneration, etc. The lack of any substantial negative side effects is also purported for most treatments. In recent years, the general public and even the medical community have increasingly accepted magnetic therapy as an alternative treatment worthy of consideration for such conditions.

Patented devices, which utilize permanent magnets to produce a time-varying magnetic field for therapeutic purposes, include Horl U.S. Pat. No. 4,727,857; Kleitz U.S. Pat. No. 5,632,720; and Souder U.S. Pat. No. 6,001,055. All of these devices function by causing permanent magnets to rotate around a fixed axis. The magnetic field generated by each of these devices sweeps out into space in a single direction. Changing the angle of the rotation requires manual manipulation of the entire device since the axis upon which the magnets rotate is stationary. It has been observed that the angle at which magnetic flux lines cut through tissue can influence the degree of beneficial effects. What is needed therefore is a handheld device or a device capable of being attached a part of the body or to clothing, or the like, that will create a sweeping magnetic field in a multitude of directions, thus providing more complete angular coverage to the part of the body being treated with the moving magnetic field.

DISCLOSURE OF INVENTION

The present invention provides a magnetic field that varies in intensity and/or in polarity by causing a magnet to rotate about two axes at the same time. This is accomplished by rotating a magnet about a first axis and concurrently or intermittently rotating this first axis around a second axis that is oblique from the first axis.

BRIEF DESCRIPTION OF DRAWINGS

FIG. 9 is a perspective view of the embodiment shown in FIG. 8 further showing an enclosure assembly 90 and retainer member 92.

FIG. 10 a perspective view of the embodiment shown in FIG. 9 from a different angle showing annular rolling surface 78 and pivot member 79.

MODE(S) FOR CARRYING OUT THE INVENTION

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
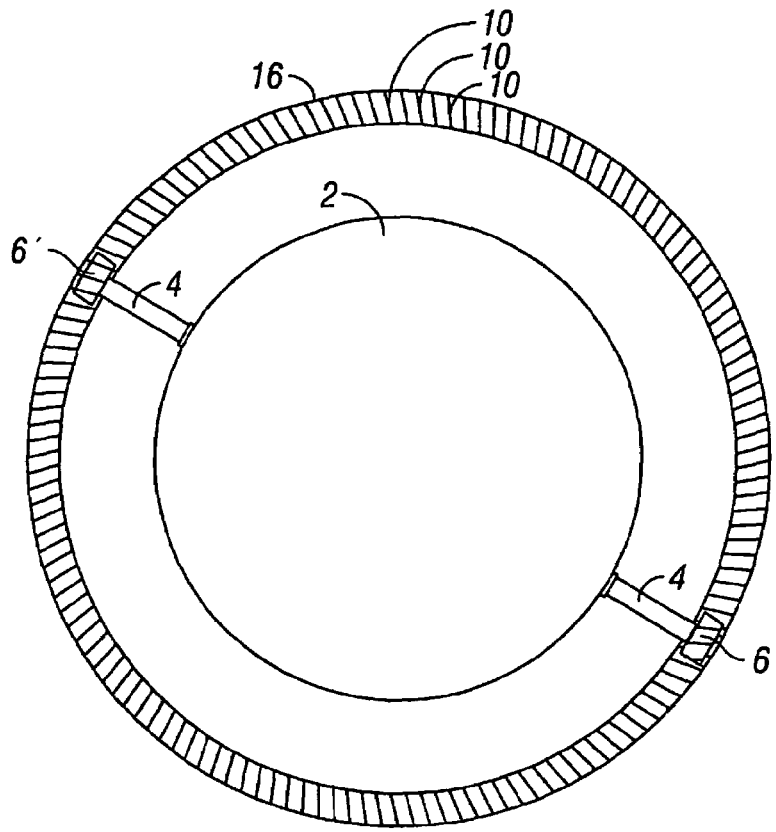
FIG. 1 is a top view of one embodiment of the pertinent features of the present invention.

One embodiment of the present invention is illustrated in FIG. 1. In this embodiment, the action of the bi-axial rotation is accomplished by mounting a permanent magnet 2 on a rod 4 that has a drive gear 6, or other meshing or traction surface arrangement, attached at one end. Although a gear system is used in the preferred embodiment, other embodiments without the use of gears can be used, such as an o-ring, sprocket, or rubberized surface capable of imposing an angular force on the rod by contact with an external force. The magnet 2, rod 4 and drive gear 6 assembly is then placed on a rotatable circular track 8, having either matching gear teeth or other surface for exerting this external force on the ends of the rod 4. The magnet 2 can be rectangular or substantially spherical in shape.

In one embodiment, rod 4 is sandwiched between the rotatable circular track 8 and a matching stationary circular track 16, which faces the rotatable circular track 8. A motor 20 is coupled to the rotatable circular track 8 and causes the track to rotate. The angular force imparted on drive gear 6 causes rod 4 to turn with track 8. Since the drive gear 6 is engaged with the surfaces of both circular tracks 8 and 16, drive gear 6 is forced to roll at the same time it moves along the circular tracks. The drive gear 6 causes rod 4 to roll like an axle in a direction perpendicular to the direction of the rotation of rod 4 around the circular tracks 8 and 16. The magnet 2 is thereby caused to move in both a primary rotational movement and a secondary rotational movement, both turning and rolling the magnet 2. As a result, this configuration creates a complex bi-axial sweeping action of the magnetic field. As shown in FIG. 1, a placeholder or floating gear 6' is placed on the end of rod 4 opposite drive gear 6 for balance and stability purposes. Floating gear 6' is rotatably mounted to rod 4 so that this gear 6' does not impart a rolling force on rod 4, and only the drive gear 6 causes rod 4 to roll.

Figure 2:
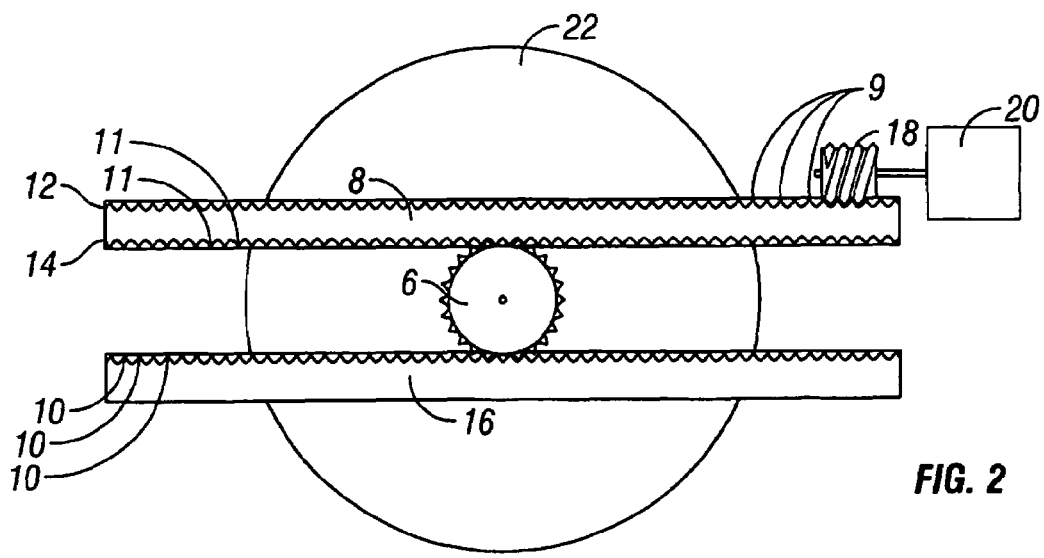
FIG. 2 is a front view of one embodiment of the present invention.

In particular, one embodiment of the present invention is shown in FIGS. 1 and 2. FIG. 1 illustrates the embodiment from a top view showing the stationary gear track 16, gear teeth 10, magnetic unit 2, the ends of rod 4, drive gear 6, and floating gear 6'. FIG. 2 shows the embodiment from a side view further showing free moving gear ring 8 and motor 20. (In FIG. 1, the free moving gear ring 8 and motor 20 have been removed for purposes of illustration of the gears 6 and 6' and stationary gear track 16.) As shown in FIG. 1, a magnetic unit 2 is mounted to a rod 4. Although the magnetic unit 2 shown in this embodiment is spherical in shape, other shaped magnets can be used such as a bar magnet, a sheet magnet having a pre-determined magnetic pattern, or the like. Additionally, although the embodiment illustrated shows rod 4 extending through magnetic unit 2, rod 4 may alternatively attach to one side or end of magnetic unit 2.

One end of the rod 4 contains a drive gear 6 that rides between a stationary gear ring 16 and free moving gear ring 8. The other end of rod 4 contains floating gear 6' which likewise rides between a stationary gear ring 16 and free moving gear ring 8. Preferably, the stationary gear ring 16 and the free moving gear ring 8 are made from a generally non-magnetic material so as not to interfere with the magnetic field produced by the magnetic unit 2. The free moving gear ring 8 has gear teeth 9 on a first surface 12 and gear teeth 11 on a second surface 14. Motor 20 drives gear 18, which in turn engages gear teeth 9 of the first surface 12 of ring 8, either directly or indirectly. Accordingly, as the gear 18 turns, it drives the free moving gear ring 8.

As the free moving gear ring 8 turns, the rod 4 is forced to turn, creating a primary rotational movement of the magnetic unit 2 because gears 6 and 6' are engaged with the gear teeth 11 on the second surface 14 of the free moving gear ring 8. End gears 6 and 6', however, also engage the teeth 10 on the surface of stationary ring 16. While floating gear 6' is rotatably mounted to one rod 4, and thereby does not impart a rolling force on rod 4, drive gear 6 is fixed to the other rod 4. As a result, when drive gear 6 is forced to roll as it rotates along free moving gear ring 8, rod 4 is forced to likewise roll about this second axis. Hence, a bi-axial rotation of magnetic unit 2 is produced, creating a complex bi-axial sweeping action of the magnetic field. With this design, only a single magnet 2 is necessary to produce this complex time-varying magnetic field. The entire embodiment can be housed inside a plastic housing (e.g., see FIGS. 5 and 11 through 15) allowing the spherical magnetic unit 2 to rotate freely about two separate axes. The present invention can be positioned or moved by hand over a desired region of the human body, or it can be attached to a part of the user's body or clothing.

In another embodiment a magnet assembly comprises a free moving member 30 having one or more extensions surrounding a magnetic unit 22. A rod 24 is mounted to the magnetic unit 22. The two ends of the rod 24 extend beyond the free moving member 30. A rolling member 26 is fixed to one end of rod 24. (Optionally, a slipping member may be rotatably mounted to the opposite end of rod 24, it has been found that, given sufficient precision of component parts, and minimization of the tolerances involved, a second floating or slipping member is not necessary.) This embodiment includes a cover 52 that surrounds the magnet assembly and has an inner surface that defines a circumferential groove that houses the rolling member 26, and that defines one or more pivot members 79 for pivotally retaining the magnet assembly. The rod 24, the rolling member 26, the free moving member 30, and the cover 52 are all preferably made of substantially non-magnetic materials.

A motor 42 or the like is coupled to an extension 36 on the free moving member 30, either directly or indirectly using a drive belt, gear box, or the like. The turning of the motor 42 then causes the magnet assembly to rotate. As the magnet assembly rotates, the rolling member and the slipping member are forced to roll due to contact with an annular surface 28 of the circumferential groove formed in the inner surface of the cover 52. This rolling action of the rolling member 26 causes the magnetic unit 22 to roll. Thus, the magnetic unit 22 both rotates about one axis and rolls about another, producing a time-varying field of magnetic flux density and a time-varying field of angular flux displacement for use in connection with humans or animals for therapeutic purposes.

Figure 3:
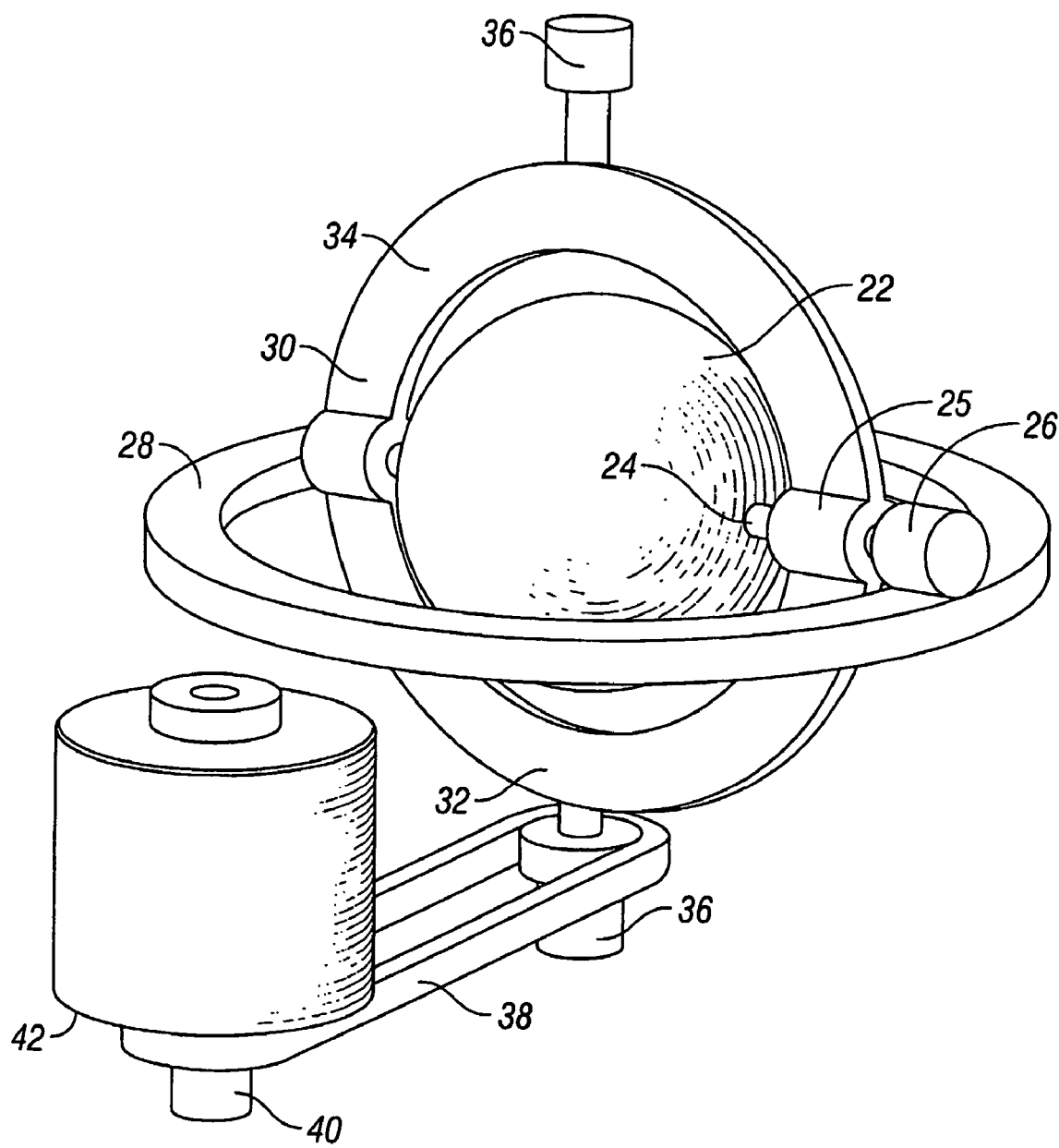
FIG. 3 is a perspective view of another embodiment of the present invention.

One example of this embodiment is shown in FIG. 3. As in the prior embodiment, the magnetic unit 22 is mounted to a rod 24. One end of the rod 24 has a rolling member 26, which is in contact with the annular surface 28. Surface 28 may be formed in the cover as described above and surrounds the magnetic unit 22. In FIG. 3, the rest of the cover has been removed so that only surface 28 is shown in the illustration. Surface 28 can also be a stationary ring with sufficient surface traction to exert an angular force on rolling member 26. The rolling member 26 and/or surface 28 would preferably consist of an elastomeric material or other material with sufficient gripping properties. Also, surrounding the spherical magnetic unit 22 is a free moving member 30, which is radially inside and oblique to surface 28. The rod 24 rotatably extends through openings 25 in the free moving member 30. As a result, when the rolling member 26 rotates along the surface 28, so does the free moving member 30, but the rolling action of the rolling member 26 does not cause the free moving member 30 to likewise roll.

Figure 5:
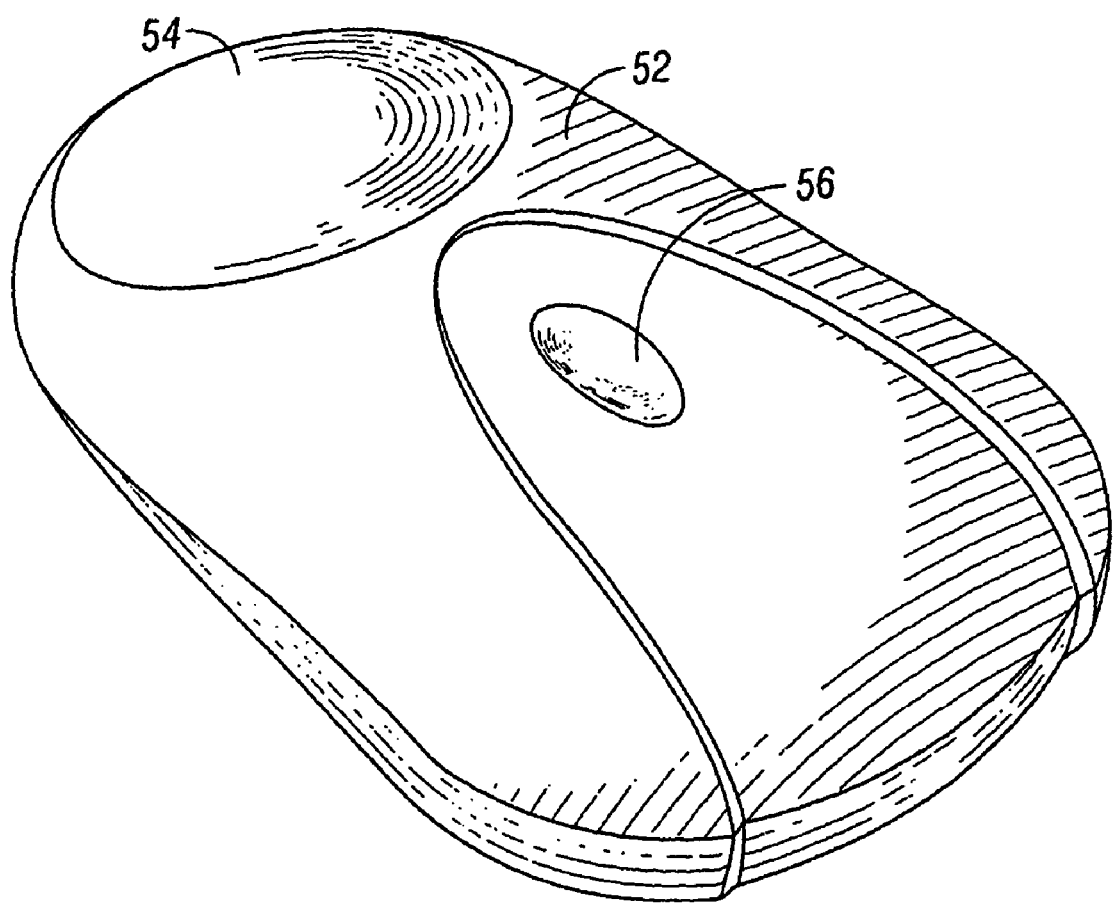
FIG. 5 is a perspective view of a cover of one embodiment of the present invention.

On each of the first half 32 and the second half 34 of free moving member 30 there exists an extension 36 that is pivotally mounted to a casing or cover 52. An example of such a cover is shown in FIG. 5, and an example of a pivot member 79 for pivotally mounting the free moving member 30 within the cover 52 is shown in FIG. 10. Attached to the extension 36 on the first half 32 of the free moving ring 30 is a drive belt 38. In this embodiment, the drive belt 38 is a rubberized belt, but can be any material with similar properties, such as a toothed belt, chain, or the like. The drive belt 38 also attaches to a rotatable unit 40 that attaches to a motor 42. Motor 42 can be a single speed motor or a motor having varying speed capabilities.

Thus, motor 42 along with rotatable unit 40 constitutes a primary rotational means, which causes magnetic unit 22 and free moving member 30 to rotate about one axis. While the free moving member 30 rotates, not only does the magnetic unit 22 rotate according to this primary rotation means, but also according to the secondary rotation means created by the interaction of rolling member 26 and annular rolling surface 28.

Figure 4:
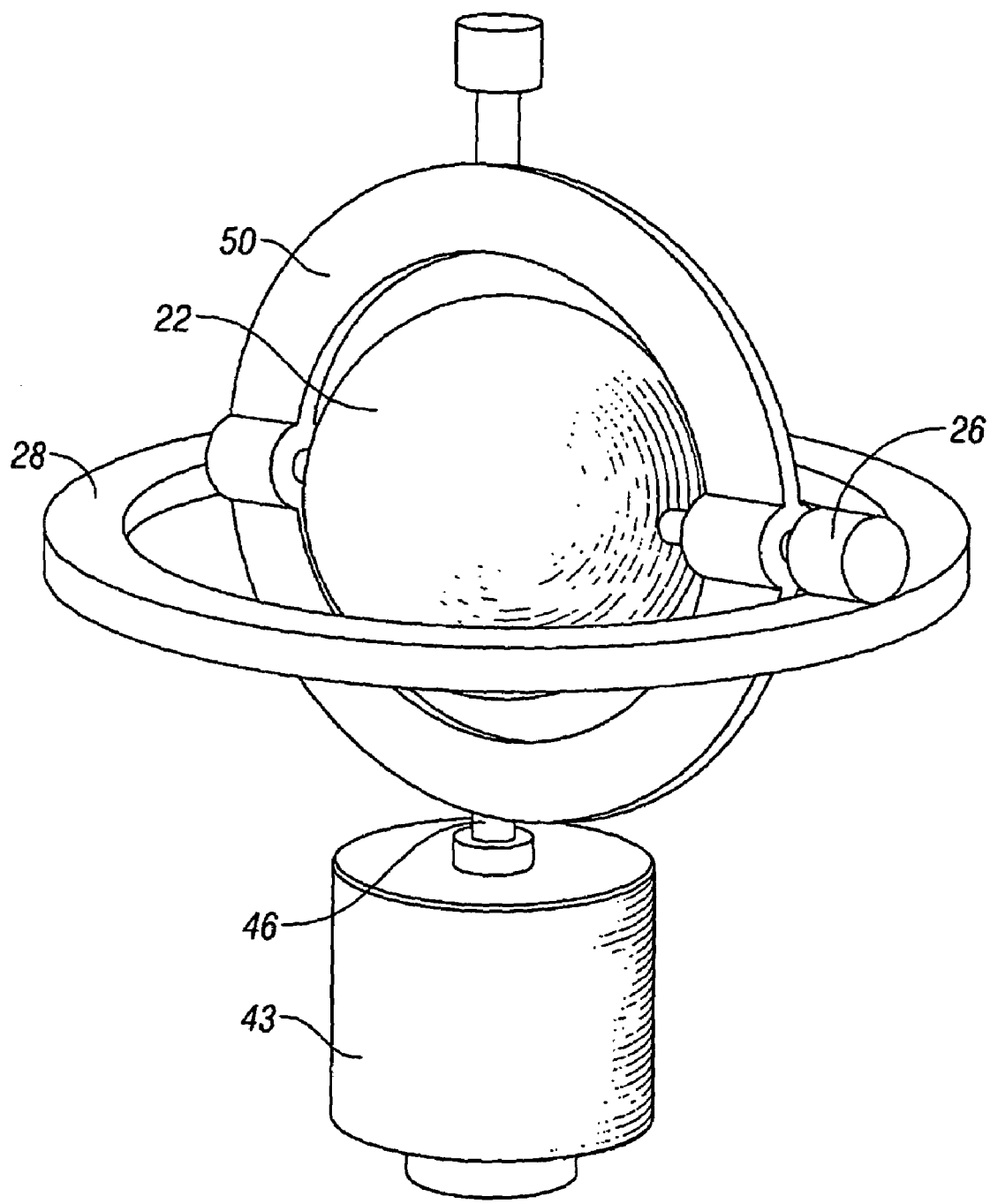
FIG. 4 is a perspective view of another embodiment of the present invention.

FIG. 4 represents yet another embodiment of the present invention. In this embodiment, a motor 43 is directly connected to the extension 46, with no need for a drive belt. The motor 43 turns the extension 46 directly, causing the free moving member 50 to rotate and having the same effect on the other parts in this embodiment as in the prior-disclosed embodiment.

FIG. 5 represents one type of cover 52 that may be used in conjunction with the presently preferred embodiments of the present invention. The cover 52 contains a power switch 56 connected to the motor (not shown). In the preferred embodiments, the cover is made of plastic, but can be made of other materials with similar generally non-magnetic properties. However, this invention can function independently without the use of the cover, or with the use of a partially transparent cover, such as window 54, so as to show the user the complex movement of the internal magnetic unit 22.

Figure 6:
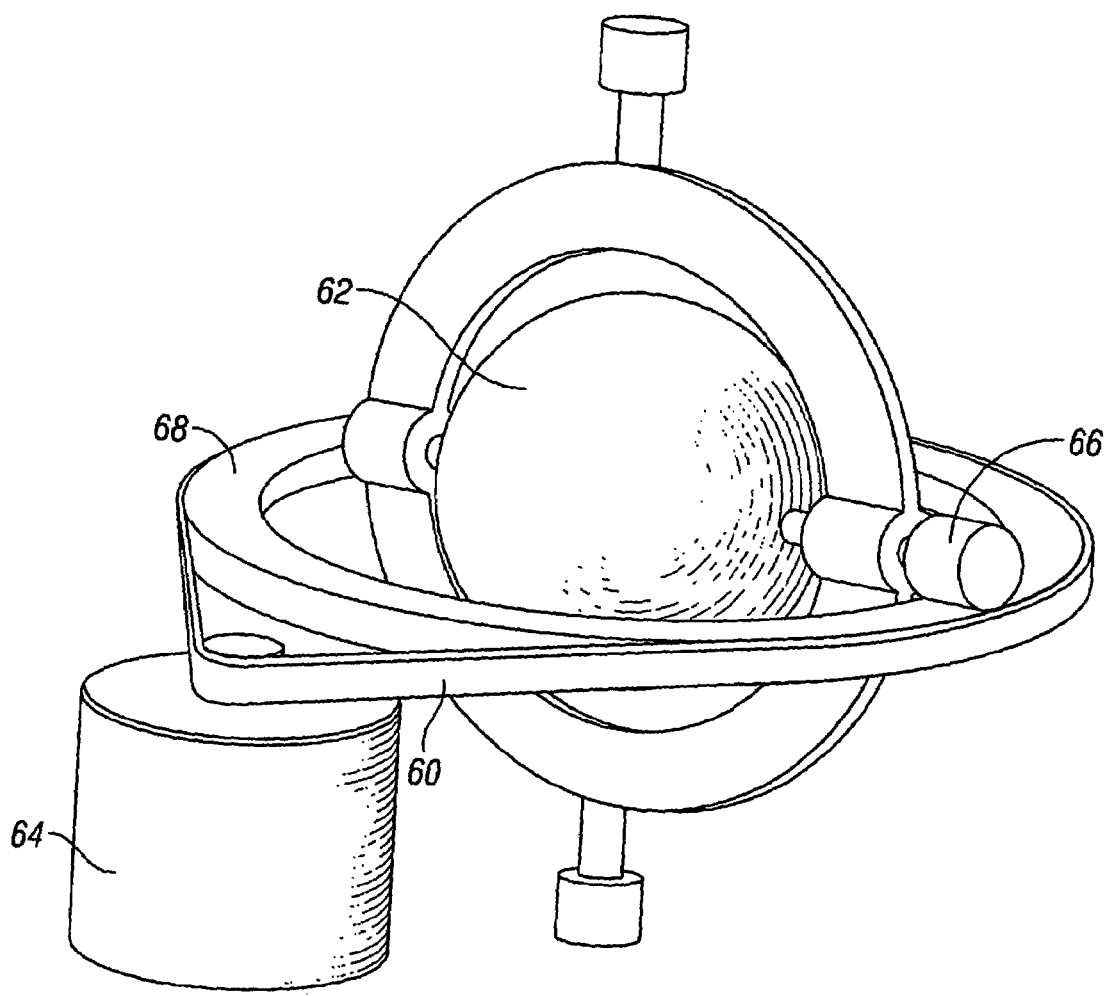
FIG. 6 is a perspective view of another embodiment of the present invention.

While FIGS. 1 and 2 illustrate one embodiment of the present invention in which gear teeth 9 and gear teeth 11 are on opposing surfaces of gear 8, other embodiments are equally contemplated by the present invention. For example, in FIG. 6, a motor 64 is in communication with the radially external surface of rotatable gear 68. As shown in FIG. 6, motor 64 causes drive belt 60 to turn gear 68, which in turn causes magnetic unit 62 to likewise turn. Magnetic unit 62 rotates as it turns because rotatable end means 66 is sandwiched between rotatable gear 68 and a fixed gear as described previously with respect to FIG. 2. The fixed gear is removed from view in FIG. 6 for purposes of clarity of the illustration. This fixed gear in combination with rotatable gear 68 causes rotatable end means 66 to rotate. As a result, magnetic unit 62, just as in FIGS. 1 and 2, rotates about two axes.

Figure 7:
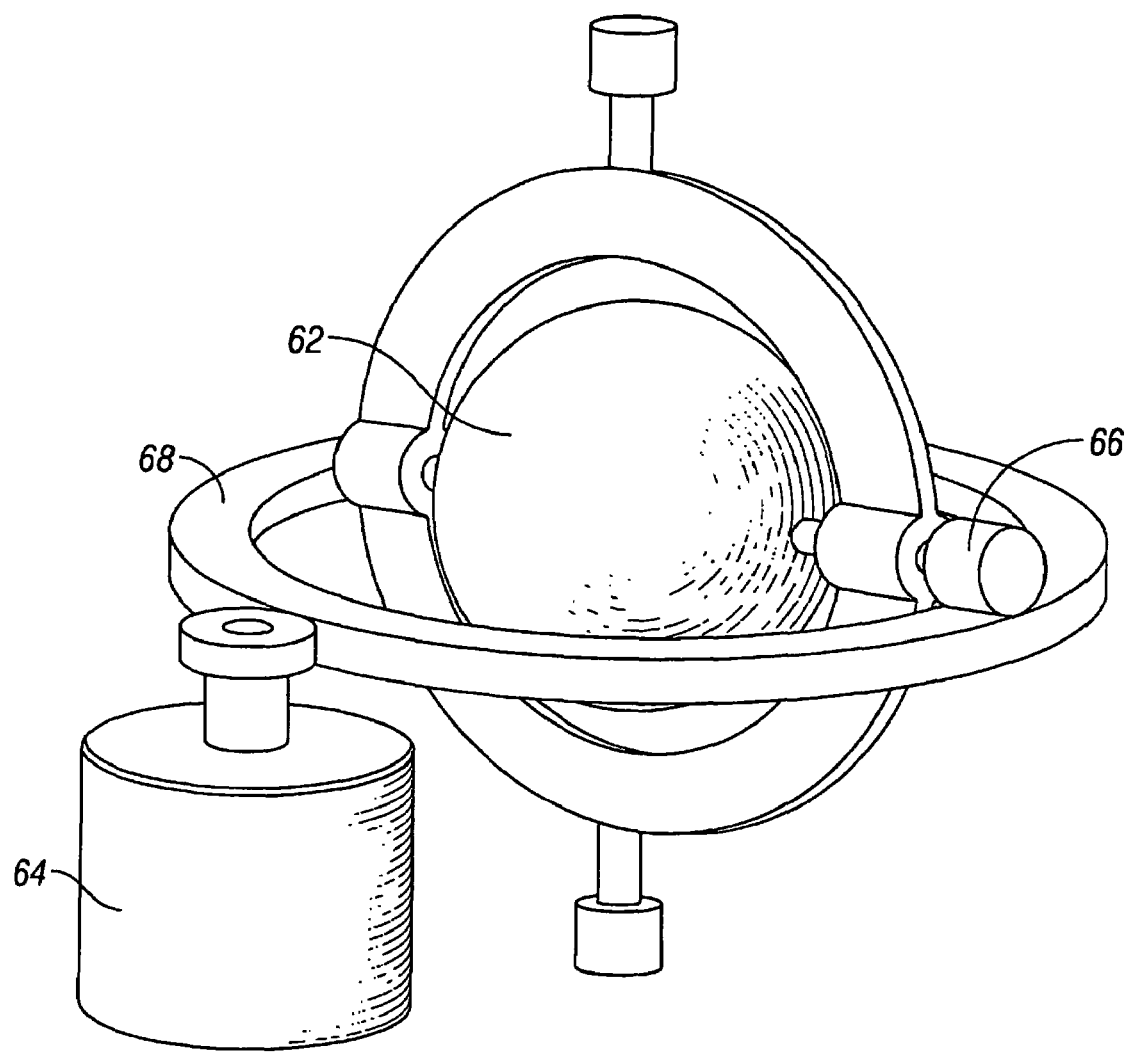
FIG. 7 is a perspective view of another embodiment of the present invention.

FIG. 6 illustrates an embodiment in which motor 64 is in communication with gear 68 indirectly, utilizing a drive belt 60. The drive belt shown is a rubberized drive belt, but could just as easily be a toothed belt, a chain, or the like, provided that the radially external surface of rotatable gear 68 comprises a matching gear, sprocket, or other friction features so that an angular force is exerted in the rotatable gear 68. Alternatively, motor 64 could be positioned so as to directly communicate with the radially external surface of gear 68 by way of an orthogonal or beveled gear and tooth configuration, or other combination of gripping surfaces as shown in FIG. 7. The result in each instance is the same; magnetic unit 62 is caused to rotate in two axes at the same time thereby causing a complex bi-axial sweeping motion of the magnetic field emanating therefrom.

Another embodiment is shown in FIGS. 8 through 15. Like in the embodiments of FIG. 3, a motor 74 (shown in FIG. 11) exerts an angular force on magnetic unit 72 while annular rolling surface 78 remains fixed relative to cover 52. As a result, the magnetic unit 72 fixed to an end rolling member 76, as described in detail above with respect to rolling member 26, is forced to both rotate about a primary axis and at the same time roll about a secondary axis. In contrast to FIG. 3, the axis of rotation of the motor is perpendicular to the primary axis of rotation of the magnet assembly.

More particularly, the magnetic unit 72 is housed inside a free moving member 80 comprising a first half 81 and a second half 83. When mating surfaces 82 and 84 of the first and second halves of the free moving member 80, the inner surface of the free moving member 80 defines an approximately spherical chamber in which the magnetic unit 72 is held. With magnetic unit 72 placed in the chamber, mating surfaces 82 and 84 are then welded together at a sufficient number of places along to withstand the sort of impacts that are common to home appliances, such as being dropped during use, etc.

Mating surfaces 82 and 84 also define one or more clearances 87. When mating surfaces 82 and 84 are welded together, these clearances 87 define openings 88. The magnetic unit 72 further comprises two protruding arms 73 which extend away from magnetic unit 72 in diametrically opposite directions and extend through and beyond two openings 88. The arms could be separate pins or rods or the like extending from the magnetic unit 82, or they could alternatively be the distal ends of a single extending rod or pin. The present invention equally contemplates a magnetic unit 72 having only a single protruding arm or pin 73 provided the magnetic unit 72 remains sufficiently stable and free to rotate about an axis defined by the elongate length of said protruding arm 73. The chamber defined by the internal surfaces of the free moving member 80 and the openings 88 defined by the clearances 87 formed in mating surfaces 82 and 84 are both large enough to loosely retain magnetic unit 72 and protruding arms 73, respectively. Thus, while magnetic unit 72 is substantially enclosed within the free moving member 80, the magnetic unit 72 is capable of freely rotating relative to the free moving member 80 about the axis of rotation defined by the one or two protruding arms 73.

The free moving member 80 is held in an enclosure assembly 90. The enclosure assembly 90 comprises an inner surface 91 which defines an approximately spherical chamber, an annular rolling surface 78 formed in inner surface 91, and a pivot member 79 disposed in the inner surface 91. Also, a portion of the inner surface 91 functions as a wave washer retaining surface, as discussed further below. The enclosure assembly 90 is preferably fixed relative to the cover 52 and thus may be mounted to the cover or integrally formed in the inner surface of the cover 52. In either case, there is sufficient clearance between the outer surface of the free moving member 80 and the inner surface 91 of the enclosure assembly 90 so that the free moving member 80 may rotate about a pivot structure 86 which is formed in the first half 81 of free moving member 80 and which pivotally engages pivot member 79. FIG. 10 illustrates an embodiment that utilizes a bearing pin as pivot member 79. This function of pivotally mounting the free moving member 80 inside the enclosure assembly 90 may likewise be accomplished by other engaging structures, such as a circular recess formed in the enclosure coupled with a point formed at the apex of the first half 81 of the free moving member 80.

As mentioned above, in a preferred embodiment, the rotation of motor 74 is perpendicular to the desired rotation of the free moving member 80. The rotary motion of motor 74 is translated by a standard right-angle gear box 75, which comprises two mating angled gears or the like. At the same time, the speed of the motor may also be stepped up or down, which will inversely affect the torque of the imparted rotary motion. Presently, the best made involves a direct current or "DC" motor connected to a right-angle step-down gear box 75 for producing a ten-fold increase in torque. The DC motor is powered by a rechargeable battery 70 housed in battery case 70' or directly from an AC/DC power converter 71 through plug-in jack 71', which may also operate as a battery recharger as is common in home appliances.

The resultant rotary force of the motor, once translated 90° and stepped down by the gear box 75, drives free moving member 80 much the same way as illustrated in and discussed with respect to FIG. 4, above. The driving shaft (not shown) extends through axial opening 89 and directly imparts an angular force on drive extension 85 located at the apex of the second half 83 of free moving member 80.

The end of one of the protruding arms 73 is equipped with rolling member 76. As free moving member 80 rotates, rolling member 76 is dragged along the annular rolling surface 78. Annular rolling surface 78 imparts an angular force on rolling member 76 as the latter moves along the annular rolling surface 78. A retainer member 92 is placed between the inner surface 91 of the enclosure assembly 90 and free moving member 80 to exert a downward axial force on free moving member 80. While the retainer member illustrated in FIG. 9 is a spring washer or wave-type washer, other means are equally contemplated for exerting an axial force on free moving member 80, such as a leaf spring, compression spring, diaphragm, or the like. This insures that a sufficient amount of contact occurs between rolling member 76 and annular rolling surface 78 to create this angular force on rolling member 76. As a result, rolling member 76 is forced to roll about the axis of its elongate dimension. A slipping member may be utilized in the opposite projecting arm 73, as described above in relation to FIGS. 3 and 4. With sufficiently tight tolerances between the magnet assembly and the enclosure assembly, however, a slipping member can be made to be unnecessary.

Figure 8:
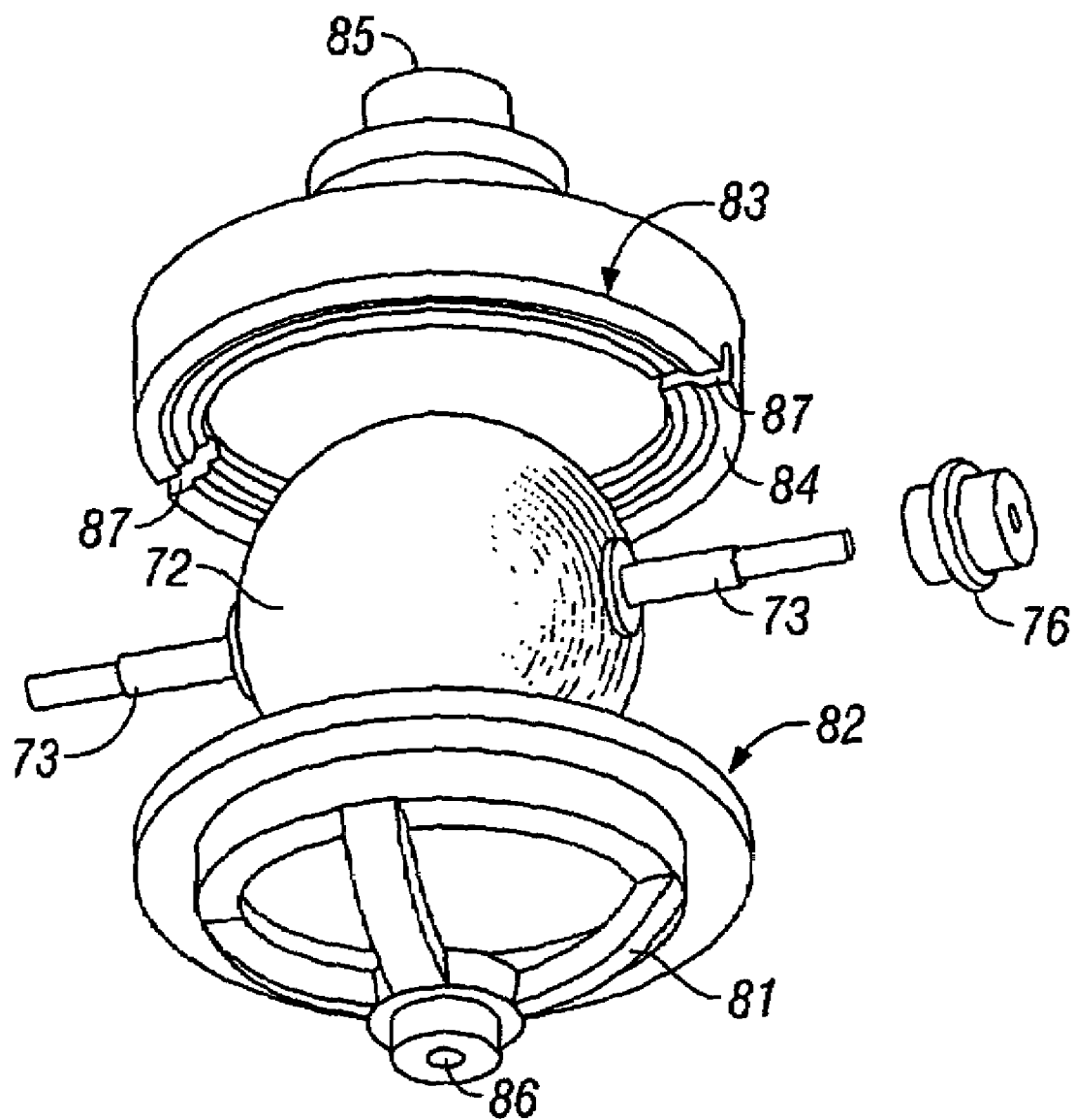
FIG. 8 is a perspective view of another embodiment of the present invention showing a magnetic unit and a free moving member.
Figure 11:
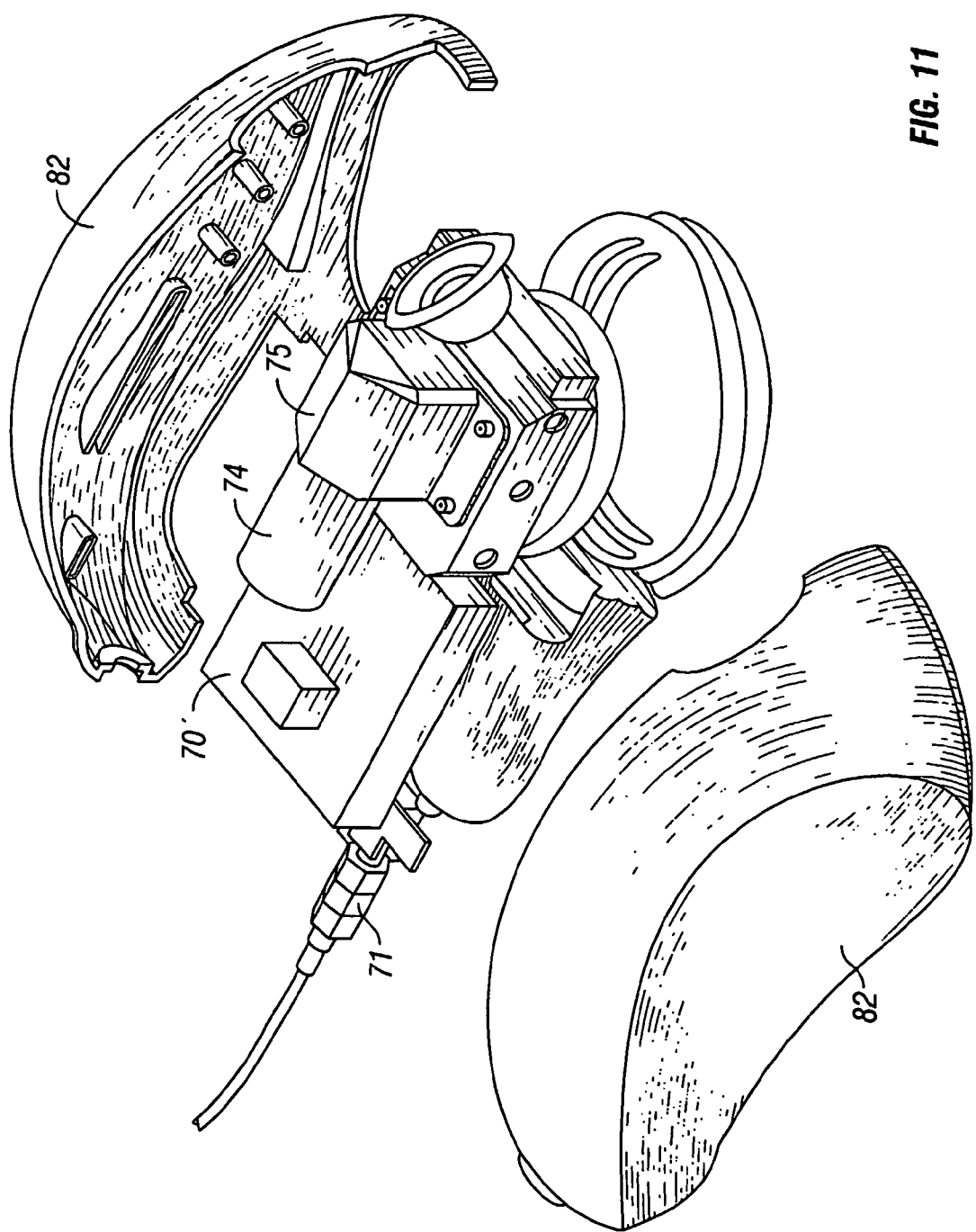
FIG. 11 is a perspective view of the embodiment FIG. 8 further showing a DC motor and right-angle gear box attached to the magnetic unit and a partially disassembled cover for enclosing the invention.

It is believed to be additionally advantageous to provide the operator with a visual means to realize the great degree of complex bi-axial movements that magnetic unit 72 is forced to make by this configuration. In FIG. 8, the first half 81 of free moving member 80 is shown as having large openings. This allows the complex movements of the magnetic unit 72 to be visible from outside the free moving member 80. It is equally contemplated that a transparent or semi-transparent material could be used to accomplish similar advantageous results. Similarly, the lower half 93 of the enclosure assembly 90 in FIG. 9 may be made from a transparent or semi-transparent material, or be formed with relatively large openings as with first half 81. A window or lens 96, as shown in FIGS. 11 through 14, may form a part of cover 94.

Figure 12:
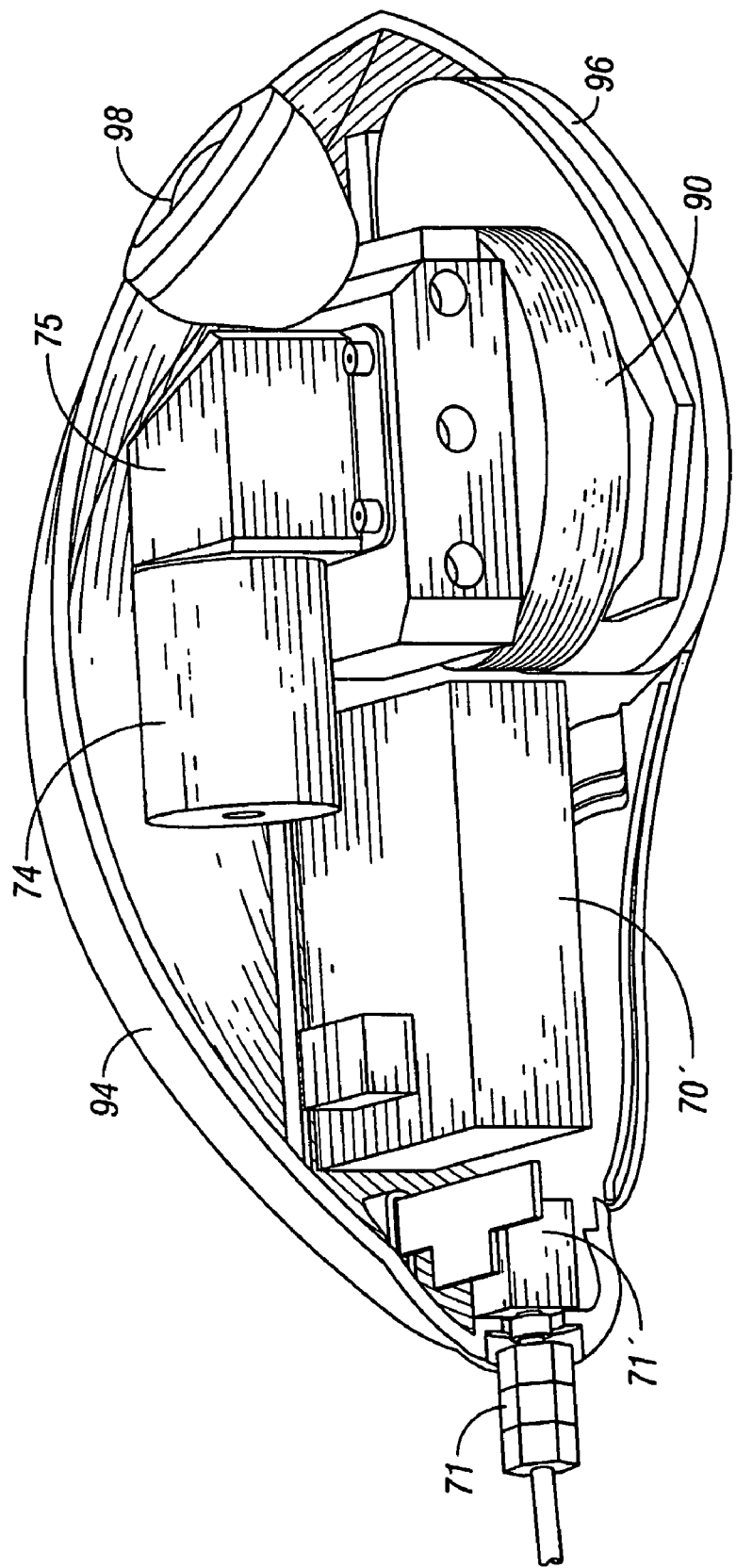
FIG. 12 is a perspective view of the embodiment FIG. 8 further showing how the component parts fit in cover 94.
Figure 13:
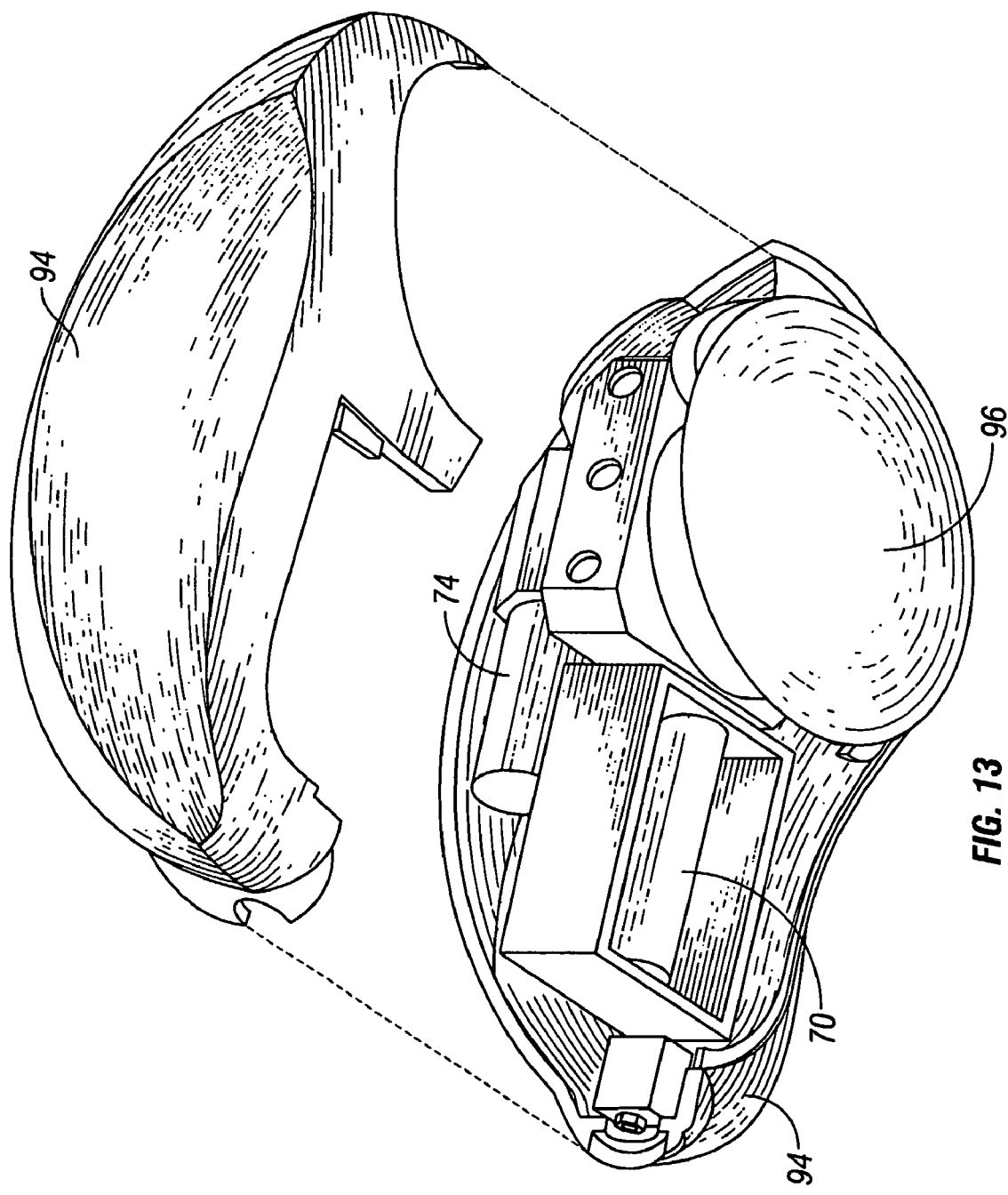
FIG. 13 is a perspective view of the embodiment shown in FIG. 12 from a different angle.
Figure 14:
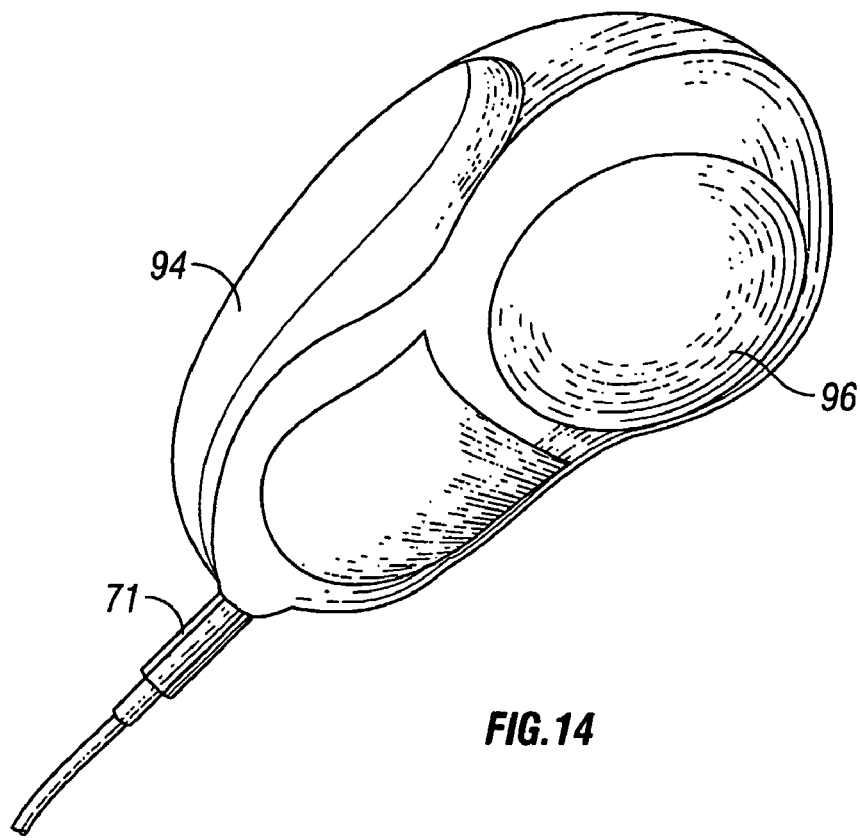
FIG. 14 is a perspective view of a cover 94 for the embodiment shown in FIG. 8.
Figure 15:
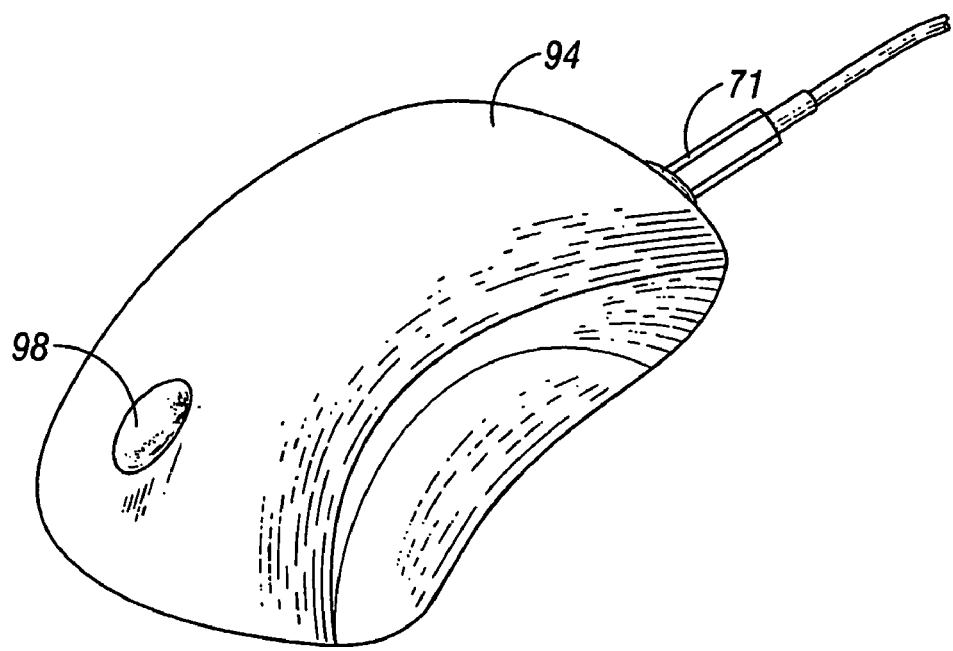
FIG. 15 is a perspective view of the cover 94 of the embodiment shown in FIG. 14 from a different angle.

In addition to the window or lens 96, the configuration shown in FIGS. 12 and 13 provide a particularly efficient packaging of the present invention. The two halves of the cover 94 are plastic and molded to fit together and capture the window or lens 96, the power switch 98, the motor 74 and gear box 75, the battery case 70', DC plug-in jack 71', and the enclosure assembly 90. That is, essentially every component of the product is captured in one of the molded cover halves, the other half therefore being capable of removal without disrupting the arrangement of the components of the invention and product. FIGS. 12 and 13 show from the top and bottom, respectively, the efficient packing of the essential and auxiliary components for the present invention in the embodiment shown. FIGS. 14 and 15 show from the bottom and top, respectively, another cover contemplated by this invention. The power/recharge cord is detachable from the product and is not necessary for proper operation of the present invention, as the motor can run on batteries 70 as shown in FIG. 13.

Again, as mentioned above, all components other than the magnet unit are preferably made out of material that will not negatively affect the magnetic flux emanating from the magnetic unit 72. Instead, it is presently believed that the proper selection of materials for the enclosure assembly may be able to positively affect the magnetic flux by concentrating the magnetic energy and refocusing it towards the body part being treated.

Figure 16:
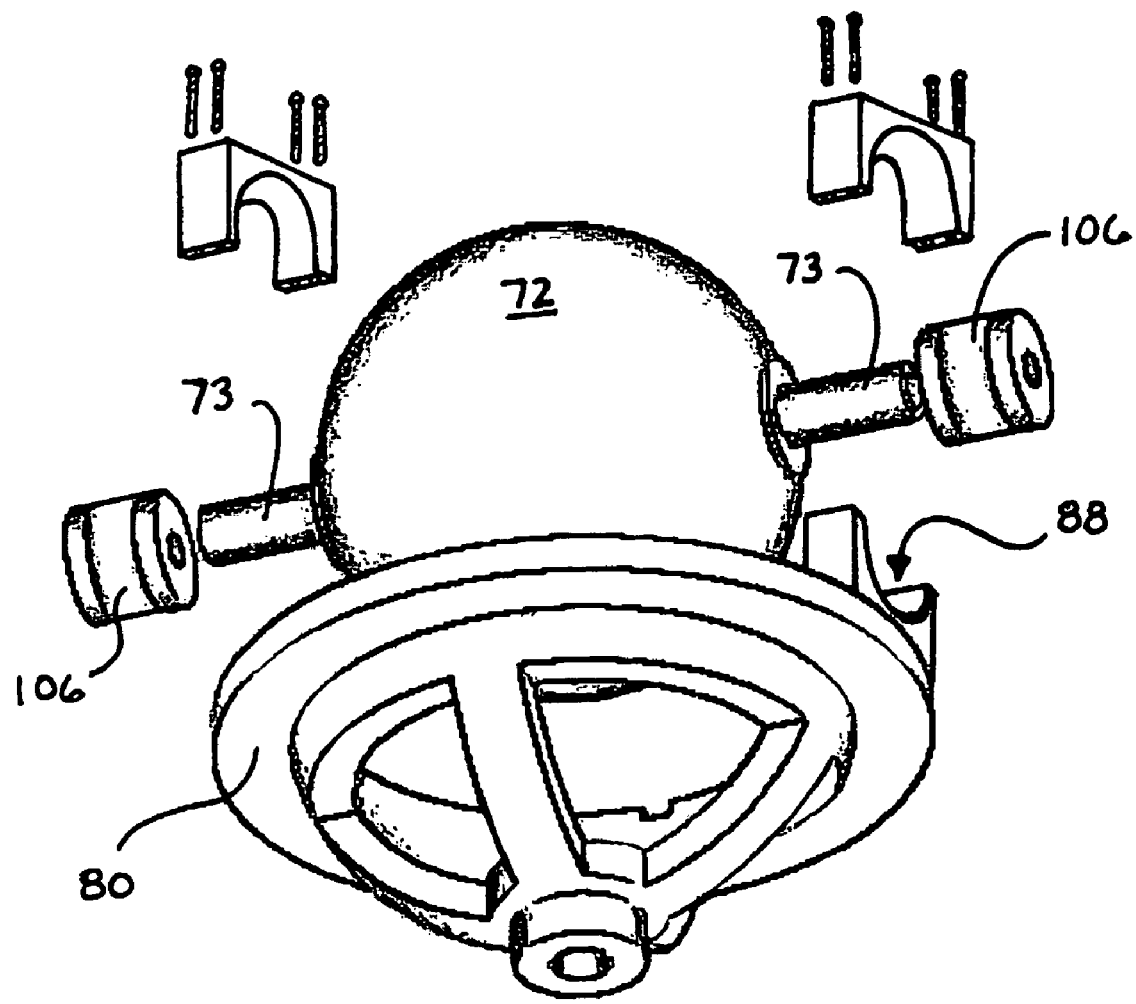
FIG. 16 is an exploded view of another embodiment of the present invention showing bearing members 106 and openings 88.
Figure 17:
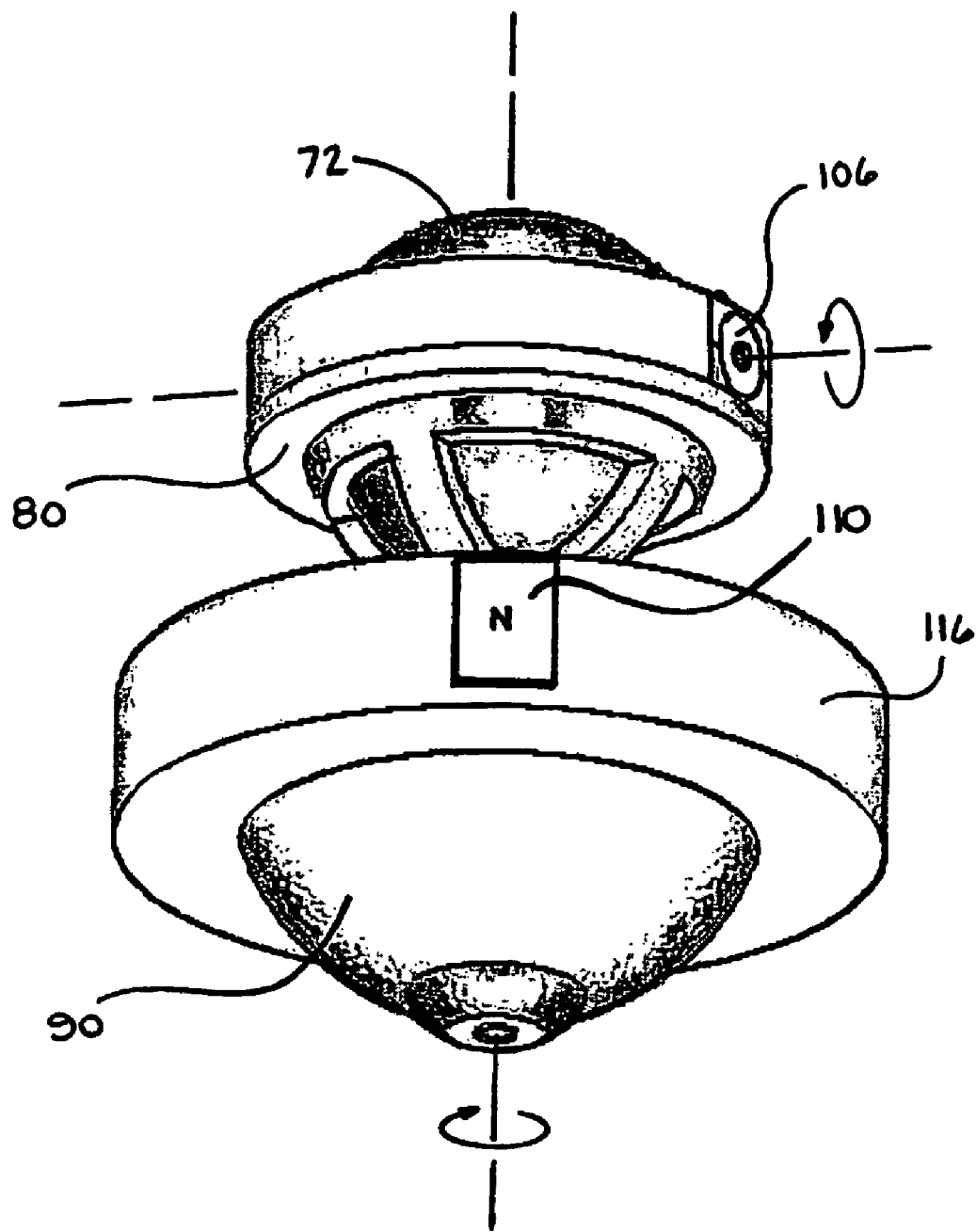
FIG. 17 is a partially exploded perspective view of an embodiment of the present invention showing a stationary magnet 110 on the stationary track 116.
Figure 18A:
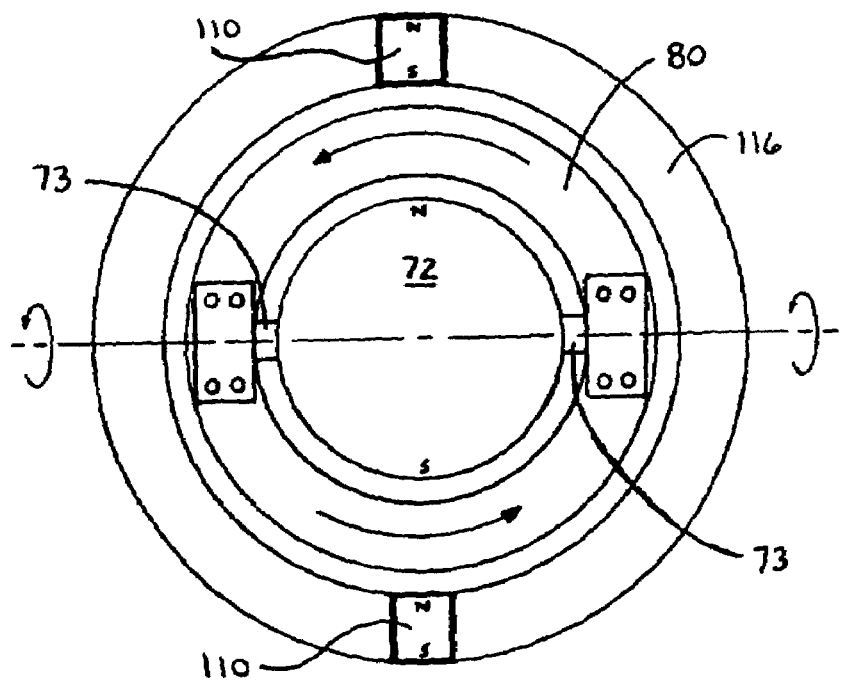
FIG. 18a is a top plan view of an embodiment of the present invention showing a stationary magnets on stationary track 116.
Figure 18B:
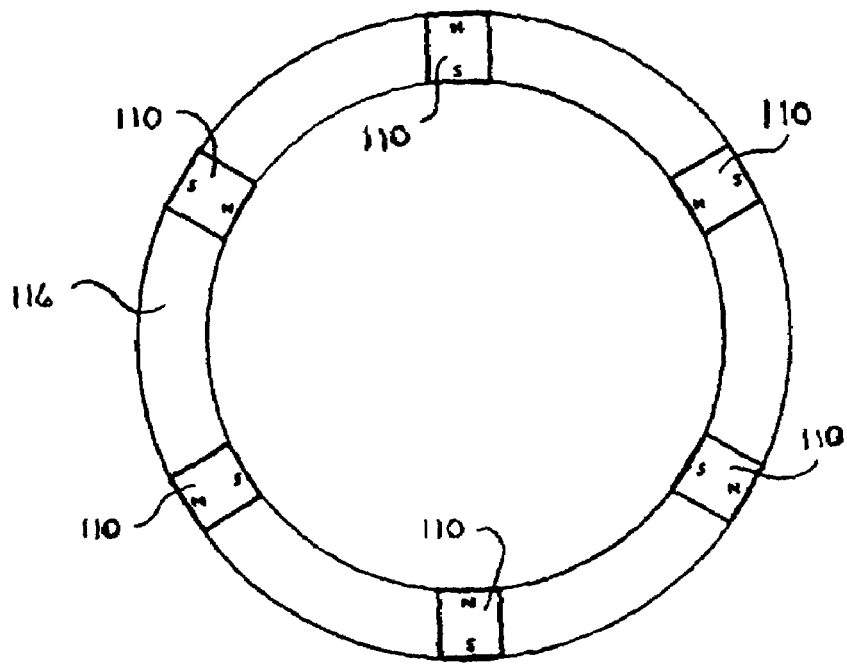
FIG. 18b is a top plan view of an embodiment of the present invention showing six (6) stationary magnets on stationary track 116.

Another embodiment of the present invention is illustrated in FIGS. 16 and 17. In this embodiment, bi-axial rotation of the magnetic body is produced by introducing a stationary magnetic field oblique to the rotation of the magnetic body. The stationary magnetic field causes the rotating magnetic body to roll about an axis of second rotation that is oblique to its axis of first rotation. The embodiment illustrated in FIG. 17 comprises at least one stationary magnet 110 fixed relative to the stationary track 116, which may typically, but not necessarily, also be fixed relative to the enclosure assembly 90.

Magnetic body 72 rotates about an axis of first rotation in concert with free moving member 80, whereas the stationary magnet or magnets 110 do not rotate with free moving member 80. Magnetic body 72 is itself mounted rotatably within free moving member 80, such as by roller bearings 106 fixed to protruding arms 73 and mounted in openings 88 of enclosure assembly 90, and thereby can rotate about an axis of second rotation. When magnetic body 72 rotates about the axis of first rotation, it encounters the magnetic field emanating from the stationary magnets 110. This fixed magnetic field interacts with the rotating magnetic field of magnetic body 72, and thereby causes magnetic body 72 to rotate about the axis of second rotation without the magnetic body 72 or its protruding arms 73 ever making physical contact with stationary track 116.

In the embodiment shown in FIGS. 16 and 17, the stationary track 116 is slightly larger in diameter than the free moving member 80, and it preferably has 1 to 8 miniature surface button magnets attached to or embedded in the wall of the track preferably being evenly spaced around the track. Each stationary magnet 110 is preferably oriented such that one of its magnetic poles is pointed in the direction of the magnetic body 72. As a result, the effect of the magnetic flux of the stationary magnets 110 on magnetic body 72 is maximized. Alternatively, the stationary track 116 may be made entirely of a magnetic material that can be singularly magnetized in an orientation oblique to the axis of first rotation or magnetized in sections of alternating polarity to produce the same effect as the separately attached button magnets discussed above on the magnetic body 72.

Consequently, magnetic body 72 rotates either intermittently or constantly about the second axis of rotation due to its interactions with the magnetic flux of the stationary magnets 110 as the magnetic body 72 is forced to rotate about the first axis of rotation by the free moving member 80. This biaxial rotation occurs without magnetic body 72 ever making physical contact with the stationary track 116 but instead only engages magnetically with the track 116 by interacting with one or a combination of stationary magnetic fields. This embodiment therefore has the added advantage of reducing the point of physical contact and thus the number of parts that encounter friction and wear and tear. The embodiment is also somewhat less noisy due to this reduction in contacting parts.

Yet another embodiment of the present invention involves placing this magnet-to-magnet interaction effect at the surface of the outwardly extending roller member. That is, a magnetic roller member, in place of the roller member 76 shown in a number of the embodiments above, may extend beyond free moving member 80 and, as it rotates about the axis of first rotation, travel in a circle just above stationary track 116. In this embodiment, the magnetic roller member comprises one or more magnets that interact with one or more stationary magnets 110 along stationary track 116 to cause the magnetic roller members to roll about the axis of second rotation. This arrangement creates the necessary magnetic coupling to turn the magnetic body 72 about the axis of second rotation while it is being rotated about the axis of first rotation.

In this embodiment, each stationary magnet 110 is preferably oriented so that one of its magnetic poles is pointed in the direction of the magnetic roller member as it passes immediately overhead. As a result the magnetic effect of the stationary magnets 110 on the magnetic roller members is maximized, and the angular force on the magnetic body 72 to cause it to rotate about the axis of second rotation is thereby maximized.

While the present invention has been described with regards to particular embodiments, it is recognized that additional variations of the present invention may be devised without departing from the inventive concept.

INDUSTRIAL APPLICABILITY

It is an object of the present invention to provide a handheld device for applying a time-varying magnetic field for use on the body of a human or animal. Another object of the present invention is providing a therapeutic device that causes the magnetic field to vary in time in more than one direction.

Another object of one embodiment of the present invention to provide a device that can be hand held or attachable to a part of a body or to clothing for applying a time-varying magnetic field to the body.

These and other objects and advantages of the present invention will be apparent from a review of the following specification and accompanying drawings.

The invention claimed is:

1. A magnetic therapeutic system, comprising:
    a magnetic unit comprising a spherical configuration;
    a free moving member rotationally coupled to said magnetic unit; and
    means for rotating said free moving member,
    said magnetic unit being contemporaneously rotatable about at least one axis by the free moving member and the rotating means acting in concert, and
    said free moving member coupled to said magnetic unit via a coupling selected from a group consisting of a gearing and a friction coupling.

2. The system of claim 1, wherein said magnetic unit further comprises a rod configured to couple to said free moving member.

3. The system of claim 2, further comprising a housing configured to enclose said magnetic unit, said free moving member, and said means for rotating.

4. The system of claim 1, wherein said magnetic unit is generally spherical.

5. The system of claim 1, wherein said free moving member is coupled to said magnetic unit via bearings.

6. A magnetic therapeutic system, comprising:
    a magnetic unit comprising a rod and a spherical configuration;
    a free moving member rotationally coupled to said magnetic unit via said rod; and
    means for rotating said free moving member,
    said magnetic unit being contemporaneously rotatable about at least one axis by the free moving member and the rotating means acting in concert, and
    said free moving member coupled to said magnetic unit via a coupling selected from a group consisting of a gearing and a friction coupling.

7. The system of claim 6, further comprising a housing configured to enclose said magnetic unit, said free moving member, and said means for rotating.

8. The system of claim 6, wherein said magnetic unit is generally spherical.

9. The system of claim 6, wherein said free moving member is coupled to said magnetic unit via bearings.

10. A magnetic therapeutic system, comprising:
    a magnetic unit comprising a rod and a spherical configuration;
    a free moving member rotationally coupled to said magnetic unit via said rod; and
    a motor coupled to said free moving member and configured to rotate said free moving member,
    said magnetic unit being contemporaneously rotatable about at least one axis by the free moving member and the motor acting in concert, and
    said free moving member coupled to said magnetic unit via a coupling selected from a group consisting of a gearing and a friction coupling.

11. The system of claim 10, further comprising a housing configured to enclose said magnetic unit, said free moving member, and said means for rotating.

12. The system of claim 10, wherein said free moving member is coupled to said magnetic unit via a friction coupling.

13. The system of claim 10, wherein said free moving member is coupled to said magnetic unit via bearings.

14. A method of providing a time-varying field of magnetic flux density, comprising:
   providing a magnetic unit;
   rotationally coupling said magnetic unit to a free moving member said rotating said free moving member is accomplished at least in part by motor; and
   rotating said magnetic unit about a second axis.

15. The method of claim 14, wherein said rotating said magnetic unit is caused at least in part by said rotating said free moving member.

* * * * *